United States Patent
Sherman et al.

(10) Patent No.: US 8,574,237 B2
(45) Date of Patent: Nov. 5, 2013

(54) METHOD AND APPARATUS FOR PREDICTING THE OPERATING POINTS OF BONE CEMENT

(75) Inventors: Jason T. Sherman, Leesburg, IN (US); Mark R. DiSilvestro, Columbia City, IN (US); Michael A. Kryger, Winnipeg (CA)

(73) Assignee: DePuy Synthes Products, LLC, Raynham, MA (US)

(*) Notice: Subject to any disclaimer, the term of this patent is extended or adjusted under 35 U.S.C. 154(b) by 2346 days.

(21) Appl. No.: 11/323,871

(22) Filed: Dec. 30, 2005

(65) Prior Publication Data

US 2007/0154874 A1    Jul. 5, 2007

(51) Int. Cl.
    *A61F 2/00*    (2006.01)
(52) U.S. Cl.
    USPC .................................. 606/92; 600/547
(58) Field of Classification Search
    USPC .................................. 606/92; 600/547
    See application file for complete search history.

(56) References Cited

U.S. PATENT DOCUMENTS

| | | |
|---|---|---|
| 3,144,966 A | 8/1964 | Cook |
| 3,413,595 A | 11/1968 | Babikov et al. |
| 3,816,811 A | 6/1974 | Cmelik |
| 4,327,587 A | 5/1982 | Docekal et al. |
| 4,338,925 A | 7/1982 | Miller |
| 4,405,249 A | 9/1983 | Scales |
| 4,461,407 A | 7/1984 | Finnegan |
| 4,546,312 A | 10/1985 | Brun et al. |
| 4,546,767 A | 10/1985 | Smith |
| 4,559,810 A | 12/1985 | Hinrichs et al. |
| 4,671,263 A | 6/1987 | Draenert |
| 4,680,958 A | 7/1987 | Ruelle et al. |
| 4,854,716 A | 8/1989 | Ziemann et al. |
| 4,862,384 A | 8/1989 | Bujard |
| 4,888,818 A | 12/1989 | Schmitt et al. |
| 4,921,415 A | 5/1990 | Thomas, III et al. |
| 4,994,065 A | 2/1991 | Gibbs et al. |
| 5,181,636 A | 1/1993 | Anderson et al. |
| 5,187,980 A | 2/1993 | Blair et al. |
| 5,431,654 A | 7/1995 | Nic |
| 5,501,374 A | 3/1996 | Laufer et al. |
| 5,556,009 A | 9/1996 | Motzko |
| 5,585,733 A | 12/1996 | Paglione |

(Continued)

FOREIGN PATENT DOCUMENTS

| | | |
|---|---|---|
| DE | 4120573 | 12/1992 |
| DE | 10008481 | 9/2001 |

(Continued)

OTHER PUBLICATIONS

"Apparatus and method for determining the consistency of bone cement" by Schreiber Translations which is a certified english translation of reference of DE 10008481 A1 above.*

(Continued)

Primary Examiner — Sean P Dougherty
Assistant Examiner — Michael C Stout
(74) Attorney, Agent, or Firm — Barnes & Thornburg LLP

(57) ABSTRACT

A method of predicting the operating state of a curable bone cement composition includes determining the impedance of the bone cement composition. The impedance is used to predict a number of operating states of the bone cement composition including end-of-work time and setting time.

33 Claims, 7 Drawing Sheets

(56) References Cited

U.S. PATENT DOCUMENTS

| | | | |
|---|---|---|---|
| 5,638,997 A | 6/1997 | Hawkins et al. | |
| 5,829,875 A | 11/1998 | Hagel et al. | |
| 5,893,488 A | 4/1999 | Hoag et al. | |
| 6,020,396 A | 2/2000 | Jacobs | |
| 6,023,170 A | 2/2000 | Hilhorst et al. | |
| 6,045,555 A | 4/2000 | Smith et al. | |
| 6,086,594 A | 7/2000 | Brown | |
| 6,155,463 A | 12/2000 | Dentler | |
| 6,161,731 A | 12/2000 | Sigg | |
| 6,227,040 B1 | 5/2001 | Hastings et al. | |
| 6,296,149 B1 | 10/2001 | Long | |
| 6,491,635 B1 | 12/2002 | Mazess et al. | |
| 6,644,122 B2 | 11/2003 | Borowczak et al. | |
| 6,736,537 B2 | 5/2004 | Coffeen et al. | |
| 6,854,349 B2 | 2/2005 | Brandhorst et al. | |
| 2003/0176807 A1* | 9/2003 | Goetz et al. | 600/547 |
| 2004/0024410 A1 | 2/2004 | Olson, Jr. et al. | |
| 2004/0267272 A1 | 12/2004 | Henniges et al. | |
| 2005/0048886 A1 | 3/2005 | Mercuri | |
| 2005/0105384 A1 | 5/2005 | Eder et al. | |
| 2005/0105385 A1 | 5/2005 | McGill et al. | |
| 2005/0119660 A1* | 6/2005 | Bourlion et al. | 606/80 |
| 2006/0000284 A1* | 1/2006 | Sherman et al. | 73/645 |
| 2006/0122623 A1 | 6/2006 | Truckai et al. | |
| 2007/0154874 A1 | 7/2007 | Sherman et al. | |
| 2008/0269761 A1* | 10/2008 | Truckai et al. | 606/94 |

FOREIGN PATENT DOCUMENTS

| | | | |
|---|---|---|---|
| DE | 10008481 A1 * | 9/2001 | |
| DE | 10008481 A1 | 9/2001 | |
| EP | 0995981 A2 | 4/2000 | |
| JP | 52-125526 | 10/1977 | |
| JP | 10179613 A | 7/1998 | |
| JP | 2001018240 A | 1/2001 | |
| JP | 2002097110 A | 4/2002 | |
| JP | 2005532196 A | 10/2005 | |
| JP | 11511247 A | 4/2011 | |
| WO | 96/10173 | 4/1996 | |
| WO | 2004014262 | 2/2004 | |
| WO | 2004075954 A2 | 9/2004 | |
| WO | WO 2005/048867 A2 | 6/2005 | |
| WO | WO 2005/048886 A2 | 6/2005 | |

OTHER PUBLICATIONS

Viano et al., "Ultrasonic Characterization of the Curing Process of Hydroxyapatite-Modified Bone Cement", *Journal of Biomedical Materials Research*, 2001, vol. 56, No. 4, pp. 593-599.

Nilsson et al., "Monitoring the Setting of Calcium-Based Bone Cements Using Pulse-Echo Ultrasound", *Journal of Materials Science: Materials in Medicine*, 2002, vol. 13, pp. 1135-1141.

Livi et al., "Dielectric Behavior at Microwave Frequencies of an Epoxy Resin During Crosslinking", *Journal of Applied Polymer Science*, 1993, vol. 50, pp. 1583-1590.

King et al., "Microwave Dynamic Dielectric Analysis of Curing Neat Resins", *Journal of Reinforced Plastics and Composites*, 1993, vol. 12, pp. 173-185.

"Tech Impedance—An Integrated Architecture for Impedance Measurement", www.sensorsmag.com, Oct. 2005, pp. 24-26.

European Search Report for European Application No. 06256545.2-2204, May 4, 2007, 6 pgs.

Japanese Search Report, Japanese Patent Application No. 2006-355236, May 9, 2012, 3 pages.

European Search Report in corresponding European patent application (i.e., EPO7 250 897), dated Jan. 12, 2009, (5 pages).

* cited by examiner

US 8,574,237 B2

METHOD AND APPARATUS FOR PREDICTING THE OPERATING POINTS OF BONE CEMENT

FIELD OF THE DISCLOSURE

The present disclosure relates generally to bone cement for use in the performance of an orthopaedic procedure.

BACKGROUND

Many orthopaedic procedures require the use of bone cement. Bone cement is used to, for example, secure a prosthetic implant to the patient's natural bone. Most bone cements include a self-curing resin formed from the blending of a liquid monomer or co-monomer with a powdered polymer or copolymer. A typical liquid monomer for use as the liquid component of bone cement is a monomeric methyl methacrylate. A typical copolymer powder for use as the powder component of bone cement is a methylmethacrylate-styrene copolymer. Curing of the bone cement composition occurs as the liquid and powder components polymerize and crosslink.

Bone cement is typically mixed in the surgical area just prior to its use. The curing of a bone cement composition is characterized by three operating points. The first of which is dough time. Dough time is distinguished qualitatively as the point in time where the bone cement no longer adheres to latex gloves. Dough time is measured relative to the initial mixing of the liquid and powder components. Dough time signifies the starting point of the working time of the bone cement composition. In other words, once dough time is reached, the bone cement composition has achieved a desired viscosity and flowability to allow for the delivery of the composition into the surgical or implant site.

The end-of-work time is the second operating point of a bone cement composition. It is distinguished qualitatively as the point in time where bone cement no longer adheres to itself. The end-of-work time is also measured relative to the initial mixing of the liquid and powder components. The end-of-work time signifies when the working time of the composition has ended. In other words, the end-of-work time indicates when the bone cement should no longer be used in the surgical procedure.

The third operating point of bone cement is setting time. It, too, is measured relative to the initial mixing of the liquid and powder components. The setting time signifies when the bone cement has cured sufficiently enough to maintain the prosthetic implant in the implant site (e.g., in the prepared bone).

SUMMARY

According to one aspect of the disclosure, a method of predicting the operating state of a bone cement composition includes sampling the electrical impedance of the bone cement composition and determining if the magnitude of the electrical impedance has decreased to a minimum impedance value. If so, a countdown timer is executed. The length of the countdown timer may be configured to predict end-of-work time and/or setting time of the bone cement composition. Setting time may also be predicted by executing a countdown timer upon the occurrence of an inflection point in the impedance magnitude data. Setting time may also be predicted by use of a countdown timer which is executed when the phase of impedance of the bone cement composition increases to a maximum phase of impedance value.

A human-detectable signal may be generated when an associated countdown timer expires thereby indicating that a particular operating state of the bone cement composition has been achieved.

According to another aspect of the disclosure, an apparatus for predicting the operating state of a curable bone cement composition includes an electrical impedance analyzer. The electrical impedance analyzer is operated to sample the electrical impedance of the bone cement composition. If the magnitude of the electrical impedance has decreased to a minimum impedance value, a countdown timer is executed. The length of the countdown timer may be configured to predict end-of-work time and/or setting time of the bone cement composition. Setting time may also be predicted by executing a countdown timer upon the occurrence of an inflection point in the impedance magnitude data. Setting time may also be predicted by use of a countdown timer which is executed when the phase of impedance of the bone cement composition increases to a maximum phase of impedance value.

A human-detectable signal may be generated when an associated countdown timer expires thereby indicating that a particular operating state of the bone cement composition has been achieved.

The above and other features of the present disclosure will become apparent from the following description and the attached drawings.

BRIEF DESCRIPTION OF THE DRAWINGS

The detailed description particularly refers to the accompanying figures in which.

DETAILED DESCRIPTION OF THE DRAWINGS

Figure 1:
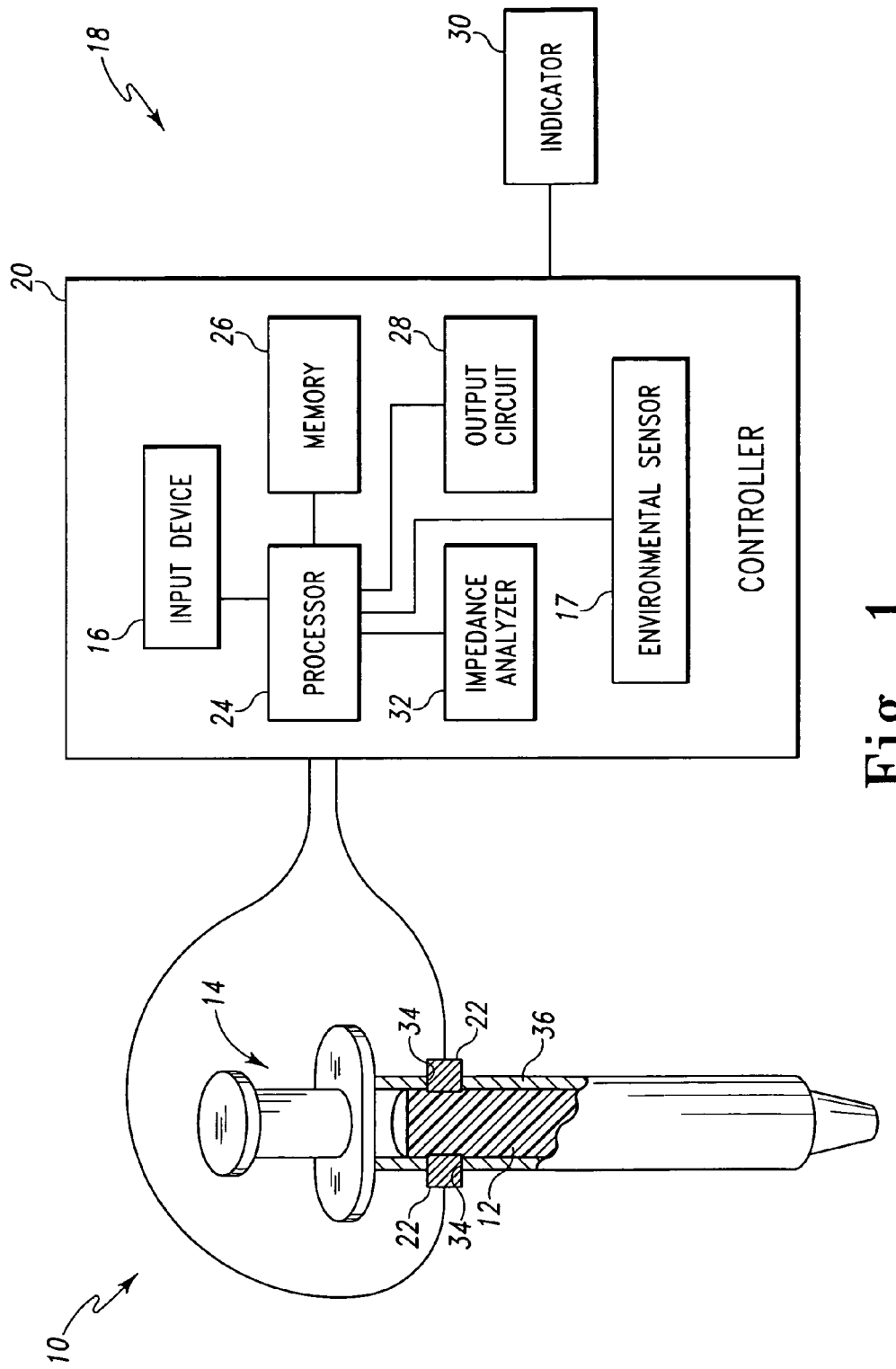
FIG. 1 is diagrammatic view of an apparatus for predicting the operating state of a bone cement composition contained in a syringe, note that a portion of the syringe has been cut away for clarity of description.

Referring now to FIG. 1, there is shown a container 10 having a curable bone cement composition 12 therein. In a known manner, the bone cement composition changes operating states over time as the composition cures. In particular, subsequent to the mixing of the liquid component and the powder component, the physical properties of the bone cement composition change over time. For example, in the case of a bone cement composition of polymethylmethacrylate, the composition polymerizes over time in a manner in which the viscosity or flowability of the composition changes (e.g., increases) until the composition is fully hardened.

The container 10 may be embodied as any type of container for containing the bone cement composition 12 as it cures. In the exemplary embodiment of FIG. 1, the container 10 is embodied as a delivery device, such as a syringe 14, for delivering the bone cement composition 12 to a surgical site (e.g., the intramedullary canal of the bone into which a prosthesis is being implanted). However, it should be appreciated that the container 10 may be embodied as any other type of container for containing the bone cement composition 12. For example, the container 10 may be embodied as the mixing apparatus (not shown) in which the liquid component and powder component is mixed. The container 10 may be embodied as a test vessel for containing a small sample of the bone cement composition 12. In such a case, subsequent to being mixed, a small portion of the bone cement composition 12 would be placed in the test vessel to be monitored in the manner described below, with the remaining amount of the bone cement composition 12 being used for the surgical procedure.

As shown in FIG. 1, a monitoring apparatus 18 is operated to monitor the operating state of the bone cement composition 12 within the syringe 14 as the composition cures. The monitoring apparatus 18 includes a controller 20 having a processor 24, a memory device 26, and output circuitry 28. The processor 24 may be any type of processor such as, for example, a microprocessor, a microcontroller, or an ASIC. The memory device 26 may be integrated with the processor 24, or may be embodied as a discrete device. The memory device 26 has stored therein the operating and/or application software necessary to operate the monitoring apparatus 18.

The output circuitry 28 of the controller 20 includes such circuitry commonly found in controllers for controlling and interacting with peripheral devices coupled thereto. For example, the output circuitry 28 includes circuitry for controlling the one or more electronically controlled indicators 30.

The indicator 30 may be embodied as a visual indicator and/or an audible indicator. In the case of a visual indicator, one or a series of light emitting diodes ("LED's") may be used. In such a case, the LED's may be illuminated to represent when the bone cement composition 12 has achieved the three operating states of interest (e.g., dough time, end-of-work time, and setting time). A tone generator or voice generator may be used as an audible indicator in a similar manner.

The controller 20 also includes an input device 16. The input device 16 may be used to identify (i.e., input) the particular type (e.g., brand and model) of bone cement composition. In exemplary embodiments, the input device 16 may be embodied as any type of keypad, touchpad, touch screen, or the like that is manipulated by a user (e.g., a surgeon). The input device 16 may also be embodied as a device that identifies the particular type of bone cement composition without direct input from the user. For example, the syringe 14 (or other container) may be equipped with a radio-frequency identification ("RFID") tag that identifies the particular type of bone cement composition within the syringe. In such a case, the input device 16 may be embodied as a radio-frequency ("RF") reader that is operable to read the contents of such an RFID tag and transmit the results to the processor 24. Yet further, in some embodiments, the controller 20 may be mechanically configured to snap or otherwise be secured to the cement delivery device (e.g., the syringe). In this case, each of the syringes of the various types of bone cement composition may be equipped with a unique electrical pad or terminal design that, when secured to the controller 20, identifies the composition.

The controller 20 also includes an environmental sensor 17 electrically coupled to the processor 24. The environmental sensor 17 is operable to sense, for example, temperature, humidity, or both. The environmental sensor 17 may be embodied as a single sensor, or may be embodied as a number of discreet sensors each of which senses a different environmental condition. By monitoring the output from the environmental sensor, the processor 24 may determine the temperature and/or humidity in the surgical operating room (or other location where the monitoring apparatus 18 is being used).

The controller 20 also includes an impedance analyzer 32. The impedance analyzer 32 is operable to determine the electrical impedance of the bone cement composition 12. In an exemplary embodiment, the impedance analyzer 32 is operable to extract both the real and imaginary components of the response signal, although in other embodiments, only the real component is extracted from the response signal. In other embodiments, the impedance analyzer 32 is operable to extract both the magnitude and phase components of the response signal. The impedance analyzer 32 may be embodied to utilize any of numerous types of impedance measurement methods such as, for example, voltage versus current methods, RF methods, or auto-balancing bridge methods. For example, the relevant circuitry from an Agilent 4294A Precision Impedance Analyzer (commercially available from Agilent Technologies of Palo Alto, Calif.) may be used. Alternatively, single chip devices such as model numbers AD5933 or AD5934 (commercially available from Analog Devices of Limerick, Ireland) may be used.

The impedance analyzer 32 may be embodied to sample at a predetermined, fixed frequency. At present, it has been found that frequencies near 1 MHz tend to produce desirable results. The monitoring apparatus 18 may also be customized for use with one or more specific types of bone cement compositions 12. Specifically, it may be that certain frequencies are more well suited for use with particular types of bone cement compositions, and, as a result, the apparatus 18 may be preconfigured to be matched with a particular type of bone cement composition. Alternatively, the impedance analyzer 32 may be adjustable to any number of different frequencies to accommodate different types of bone cement compositions. In such a case, the impedance analyzer 32 may be configured with a number of preset frequencies which correlate to a number of the more common bone cement compositions. Yet further, the impedance analyzer 32 may be configured to sweep a frequency range with the results of the sweep being correlated in a desired manner.

As shown in FIG. 1, a pair of terminals 22 is used to sample the impedance of the bone cement composition 12. The terminals 22 may be integrated in the design of the container 10 (e.g., integrated into the design of the syringe 14). In one exemplary embodiment, the terminals 22 extend through a pair of openings 34 in the sidewall 36 of the syringe 14. In such a way, the terminals 22 are placed in direct contact with the bone cement composition 12. It should be appreciated that other arrangements are also contemplated. For example, the terminals 22 may be secured to the syringe 14 in a manner in which the sidewall 36 is positioned between the terminals 22 and the bone cement composition 12. In such a case, the terminals 22 indirectly contact the bone cement composition 12 (i.e., are not in direct contact with the composition). Filtering calculations may be used to remove the component of the measured impedance associated with the sidewall 36 of the syringe 12.

Figure 2:
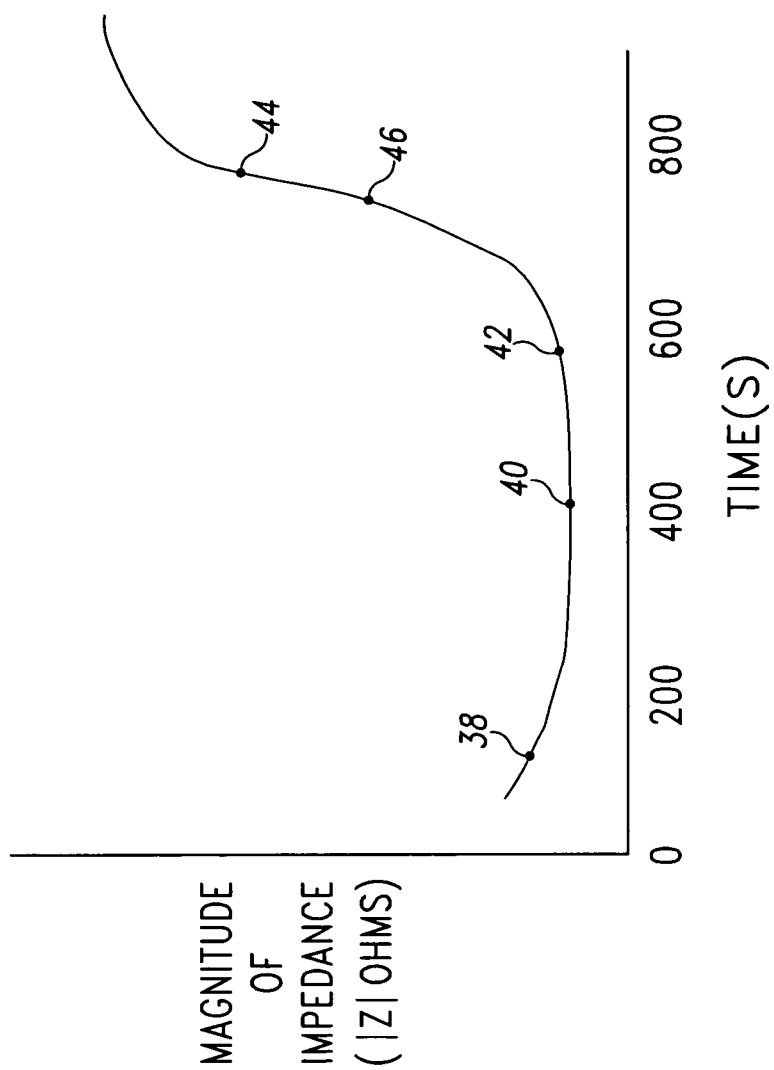
FIG. 2 is a graph showing a plot of the magnitude of the electrical impedance of a bone cement composition versus time.

The impedance analyzer 32 may be operated to sample the impedance of the bone cement composition 12 as the composition cures with the output of the analyzer 32 being stored in the memory device 26. In such a way, historical impedance data can be stored and analyzed. The analyzed data may be used as a tool for predicting end-of-work time and setting time of the bone cement composition 12. An exemplary magnitude of impedance versus time plot is shown in FIG. 2. As can be seen from the plot, as the bone cement composition cures, impedance magnitude decreases to a minimum point (shown as point 40 on the plot). Thereafter, the magnitude of impedance increases until it reaches a steady state. As will be discussed below in more detail, end-of-work time (shown as point 42 on the plot) may be predicted by determining when the measured impedance magnitude reaches a minimum value, and thereafter commencing a countdown timer. When the countdown timer expires, the end-of-work time of the bone cement composition 12 has been achieved. It should be appreciated that the length of the timer may be varied based upon, for example, the type of bone cement composition and environmental factors.

In order to determine the point of minimum impedance magnitude, the memory device 26 is used as a data buffer for storing historical data related to the magnitude of the electrical impedance of the bone cement composition 12. For example, the point of minimum impedance magnitude may be determined by storing historic impedance magnitude data in the memory device 26 and comparing the current magnitude of impedance value to stored values. Such historic data may be stored in a simple first-in first-out (FIFO) data buffer. It should be appreciated that a smoothing filter may be used to smooth the raw data. For example, a center-weighted smoothing filter may be applied to the raw data set to facilitate the determination of the minimum magnitude of impedance value. One such center-weighted smoothing filter that has shown to be effective for removing noise, while still maintaining the original signal trend, is as follows (where |Z| is the magnitude of impedance):

$$|Z_o|(t_0) = \frac{|Z|(t_{-2}) + 2|Z|(t_{-1}) + 4|Z|(t_0) + 2|Z|(t_1) + |Z|(t_2)}{10}.$$

The point of minimum magnitude of impedance may also be determined by identifying local minimums, or the area of the curve around local minimums, in a plot of magnitude of impedance versus time. For example, the first derivative of the magnitude of impedance versus time plot may be tracked. When the first derivative is zero, a local minimum has been achieved. Identification of this local minimum may be used to determine when the magnitude of impedance has reached a minimum value. It should be appreciated that a smoothing filter may also be used to remove noise from the calculations associated with the first derivative of the magnitude of impedance versus time plot. In one exemplary embodiment, the backwards difference approximation method is used to generate a discrete derivative approximation using the following equation:

$$\frac{d|Z|(t_z)}{dt} = \frac{|Z|(t_z) - |Z|(t_{z-1})}{t_z - t_{z-1}}.$$

The result of this equation is filtered using a median filter with a window of three data points to smooth the results using the following equation:

$$y(t_z) = \left[ \text{median}\left( \frac{d|Z|(t_{z-1})}{dt}, \frac{d|Z|(t_z)}{dt}, \frac{d|Z|(t_{z+1})}{dt} \right) \right].$$

As described above, a countdown timer may be triggered in response to determination of the point of minimum magnitude of impedance. It should also be appreciated that the countdown timer may be triggered by methodologies used to locate the point of minimum magnitude of impedance, but not actually triggered by the point of minimum magnitude of impedance itself. For example, as described above, the first derivative of the magnitude of impedance versus time plot may be tracked with a local minimum being achieved when the first derivative reaches zero. However, the countdown time may be initiated when the first derivative has decreased to a value within a predetermined threshold of zero. Alternatively, the countdown timer may be triggered once the first derivative has reached zero and started to increase, but is still within a predetermined threshold of zero. In other words, the countdown timer may be triggered when the measured magnitude of impedance falls within a predetermined range on either side of the curve of the point of minimum magnitude of impedance. Through experimentation, the length of the countdown timer may be adjusted to accommodate any such variations. Similar methods may also be used in the case of determining minimum magnitude of impedance via the use of a buffer (e.g., a FIFO buffer). As such, it should be appreciated that as used herein, the phrase "if the magnitude of electrical impedance has decreased to a minimum value" is intended to cover not only if the actual minimum has been achieved, but also if a technique for determining the minimum magnitude of impedance has been used and the output of such a technique is within a predetermined threshold of the minimum magnitude of impedance value.

It should also be appreciated that the countdown timer may be implemented by use of a system clock, a real time clock, or other clock used to drive a counter. Although described conventionally as a countdown timer, it should be appreciated that the timer may count up or count down. The countdown timer may be implemented through hardware, software, firmware, or some combination thereof.

In addition to end-of-work time, setting time may also be predicted by determining when the measured magnitude of impedance reaches a minimum value, and thereafter commencing a countdown timer. In particular, it has been found that setting time usually occurs within some predictable period of time subsequent to when the measured magnitude of impedance reaches its minimum value. As such, a setting time countdown timer may be commenced when the measured magnitude of impedance reaches a minimum value. When such a countdown timer expires, the setting time of the bone cement composition 12 has been achieved. It should be appreciated that the length of the timer may be varied based upon, for example, the type of bone cement composition and environmental factors. Moreover, it should also be appreciated that the timer used to predict setting time of the composition 12 may be the same timer as the one used to predict end-of-work time (since they both commence when the measured magnitude of impedance reaches a minimum value). In such a case, a first signal is generated when the timer reaches a point associated with end-of-work time, and a second signal is generated when the timer reaches a point associated with setting time. Alternatively, separate countdown timers may be used for end-of-work and setting time. Such a separate setting time countdown timer may commence when the measured magnitude of impedance reaches a minimum value (and hence run concurrently with the end-of-work timer up to the end-of-work time), or, alternatively, may commence at end-of-work time.

The output of the impedance analyzer 32 may also be used to determine the setting time of the bone cement composition 12 in other manners. For example, as shown in the plot of FIG. 2, as the magnitude of electrical impedance increases from its minimum value (at point 40 on the plot), an inflection point 46 is encountered on the curve. It has been found that setting time may be predicted by determining when such an inflection point is encountered, and thereafter commencing a countdown timer. When the countdown timer expires, the setting time of the bone cement composition 12 has been achieved. It should be appreciated that the length of the timer may be varied based upon, for example, the type of bone cement composition and environmental factors.

To do so, the second derivative of the magnitude of impedance data is calculated. The inflection point 46 on the curve is encountered with the second derivative changes signs. The following equation was used to find the first derivative:

$$\frac{d|Z|(t_o)}{dt} = \frac{|Z|(t_1) - |Z|(t_o)}{t_1 - t_o}.$$

The results of this were then used to find the second derivative using the following equation:

$$\frac{d^2|Z|(t_o)}{dt^2} = \left(\frac{d|Z|(t_1)}{dt} - \frac{d|Z|(t_o)}{dt}\right) / (t_1 - t_o).$$

It should be appreciated that other well known methods for numerically determining the first and second derivative of a function may also be used.

Figure 3:
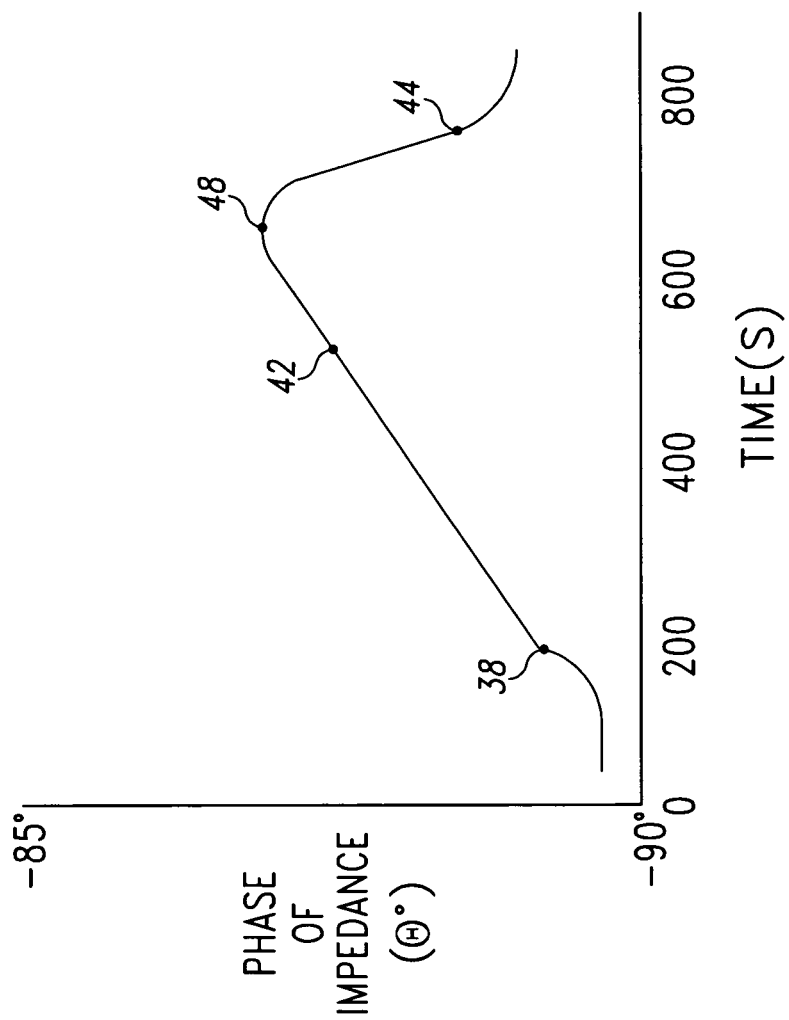
FIG. 3 is a graph showing a plot of phase of impedance of a bone cement composition versus time.

As discussed above, the impedance analyzer 32 may also be operated to sample the phase of impedance of the bone cement composition 12 as the composition cures. In such a way, historical phase of impedance data can be stored and analyzed. The analyzed data may be used as a tool for predicting setting time of the bone cement composition 12. An exemplary phase of impedance versus time plot is shown in FIG. 3. As can be seen from the plot, as the bone cement composition cures, phase of impedance increases to a point of maximum impedance (shown as point 48 on the plot). Thereafter, phase of impedance decreases until it reaches a steady state. Setting time may be predicted by determining when the measured phase of impedance reaches a maximum value, and thereafter commencing a countdown timer. When the countdown timer expires, the setting time of the bone cement composition 12 has been achieved. It should be appreciated that the length of the timer may be varied based upon, for example, the type of bone cement composition and environmental factors.

The point of maximum phase of impedance may be determined in similar manners as the point of minimum impedance. For example, the memory device 26 may be used as a data buffer for storing historical data related to the phase of impedance of the bone cement composition 12. Such historic phase of impedance data may then be compared to the current phase of impedance value to determine if the maximum value has been achieved. Such historic data may be stored in a simple first-in first-out (FIFO) data buffer. It should be appreciated that a smoothing filter may be used to smooth the raw data. For example, a center-weighted smoothing filter may be applied to the raw data set to facilitate the determination of the maximum phase of impedance value. The point of maximum phase of impedance may also be determined by identifying local maximums, or the area of the curve around local maximums, in a plot of phase of impedance versus time. For example, the first derivative of the phase of impedance versus time plot may be tracked. When the first derivative is zero, a local maximum has been achieved. Identification of this local maximum may be used to determine when the phase of impedance has reached a maximum value. It should be appreciated that a smoothing filter may also be used to remove noise from the calculations associated with the first derivative of the phase of impedance versus time plot.

As described above, a countdown timer may be triggered in response to determination of the point of maximum phase of impedance. It should also be appreciated that the countdown timer may be triggered by methodologies used to locate the point of maximum phase of impedance, but not actually triggered by the point of maximum phase of impedance itself. For example, as described above, the first derivative of the phase of impedance versus time plot may be tracked with a local maximum being achieved when the first derivative reaches zero. However, the countdown time may be initiated when the first derivative has increased to a value within a predetermined threshold of zero. Alternatively, the countdown timer may be triggered once the first derivative has reached zero and started to decrease, but is still within a predetermined threshold of zero. In other words, the countdown timer may be triggered when the measured phase of impedance falls within a predetermined range on either side of the curve of the point of maximum phase of impedance. Through experimentation, the length of the countdown timer may be adjusted to accommodate any such variations. Similar methods may also be used in the case of determining maximum phase of impedance via use of a buffer (e.g., a FIFO buffer). As such, it should be appreciated that as used herein, the phrase "if the phase of electrical impedance has increased to a maximum value" is intended to cover not only if the actual maximum has been achieved, but also if a technique for determining the maximum phase of impedance has been used and the output of such a technique is within a predetermined threshold of the maximum phase of impedance value.

The monitoring apparatus 18 may be programmed to predict the operating state of the bone cement composition 12 within the syringe 14. In particular, an experimental test may be conducted to gather empirical data relating to, for example, each of the three operating states of interest (e.g., dough time, end-of-work time, and setting time) of a particular bone cement composition 12. In such an experimental test, the composition 12 may be sampled to determine the characteristic amount of time that lapses from when the minimum magnitude of impedance value is measured prior to the end-of-work time and setting time. Similar tests may also be used to determine the amount of time that lapses from when an inflection point is reached on the plot (after the minimum impedance magnitude value as been achieved—i.e., as the plot is rising in FIG. 2) to when setting time is achieved. Other experimental tests may be conducted to determine the amount of time that lapses from when the maximum phase of impedance value is measured to when setting time is achieved. It should be appreciated that each or all of such tests may be performed for various different types of bone cement compositions, in various different environmental conditions, and at various frequencies. Simplified, filtered plots of the results of experimental tests for a particular type of bone cement composition is shown in FIGS. 2 and 3. As shown in the graph if FIG. 2, from dough time (shown as point 38), the magnitude of the impedance of the bone cement composition 12 decreases until it reaches its minimum value (shown as point 40). From there, the magnitude of impedance rises through end-of-work time (shown on the plot as point 42). The amount of time between when the minimum value is achieved and when end-of-work time occurs can be empirically determined during the test. The magnitude of impedance plateaus as the composition undergoes the physical phase change associated with setting time (setting time is shown as point 44 on the plot). The amount of time between when the minimum magnitude of impedance value is achieved and when setting time occurs can be empirically determined during the test. Moreover, the amount of time between the first inflection point on the plot beyond when the minimum value is obtained (such an inflection point is shown as point 46 on the plot) and setting time can also be empirically determined during the test. The plot of the phase of impedance versus time is shown in FIG. 3 with dough time, end-of-work time and setting time being designated with the same reference numerals as those used in FIG. 2 (i.e., reference numerals 38, 42, and 44, respectively). In the case of the plot of FIG. 3, the amount of time between when the maximum phase impedance value is achieved (shown as point 48 on the plot of FIG. 3) and when setting time occurs can be empirically determined during the test. This plot was created using initial empirical data.

Exemplary empirically determined time values are shown in Table 1 below. In this case, the bone cement compositions were mixed using a vacuum cartridge mixing system which is commercially available from DePuy Orthopaedics, Inc. of Warsaw, Ind. Five different types of bone cement compositions were tested, including medium viscosity (MV), medium viscosity with gentamicin (GMV), high viscosity (HV), high viscosity with gentamicin (GHV), and fast setting high viscosity (FS). Each of these types of compositions corresponds to commercially available cements from DePuy including SmartSet MV, SmartSet GMV, SmartSet HV, SmartSet GHV, and DePuy-2 bone cements, respectively. Each of the tests was performed at 20° C. The first data column reflects the average time and the standard deviation for the time between determination of the point of minimum magnitude of impedance to end-of-work time. The second data column reflects the average time and the standard deviation for the time between determination of the point of minimum magnitude of impedance to setting time. The third data column reflects the average time and the standard deviation for the time between determination of the inflection point to setting time.

TABLE 1

| Cement Type | Min|Z| to EOW (s) | Min|Z| to SET (s) | Inflect to SET (s) |
|---|---|---|---|
| MV | 108 ± 13 | 271 ± 17 | 76 ± 48 |
| GMV | 135 ± 27 | 328 ± 43 | 116 ± 45 |
| HV | 35 ± 19 | 193 ± 123 | 27 ± 34 |
| GHV | 38 ± 32 | 248 ± 28 | 26 ± 33 |
| FS | 42 ± 13 | 152 ± 35 | 22 ± 36 |

Empirically determined time values may be programmed in the controller 20 for use during a surgical procedure. Specifically, as will be described below in greater detail, during a surgical procedure, the electrical impedance of the bone cement composition 12 may be repeatedly determined over time (e.g., sampled) by the apparatus 18. Such sampled values may then be analyzed to determine when the minimum magnitude of impedance value has been achieved. As described above, once the minimum magnitude of impedance value has been achieved, a countdown timer is commenced, with end-of-work time being achieved at the end of the countdown timer. The empirically determined time values for a given cement composition in known environmental conditions are used to determine the length of such a countdown timer. For example, the empirically determined amount of time between when the minimum magnitude of impedance value is achieved and end-of-work time is used as the length of the associated countdown timer. Similar empirically generated time values can also be used for the countdown timers associated with setting time. The length of any of the various countdown timers may be altered based on the input received by the input device 16 and the output of the environmental sensor 17 since the amount of time between when the minimum impedance magnitude value is achieved and end-of-work time or setting time may be dependent on the type of bone cement composition being used and environmental conditions.

In addition to such threshold determination of end-of-work time and setting time, the empirical values may also be used as a predictive tool. For example, the "time remaining" may be presented to the surgeon as the countdown timer continues to approach its duration. Such a tool would be useful for informing the surgeon of the amount of time remaining before the cement delivery phase of the surgical procedure should be completed.

Figure 4:
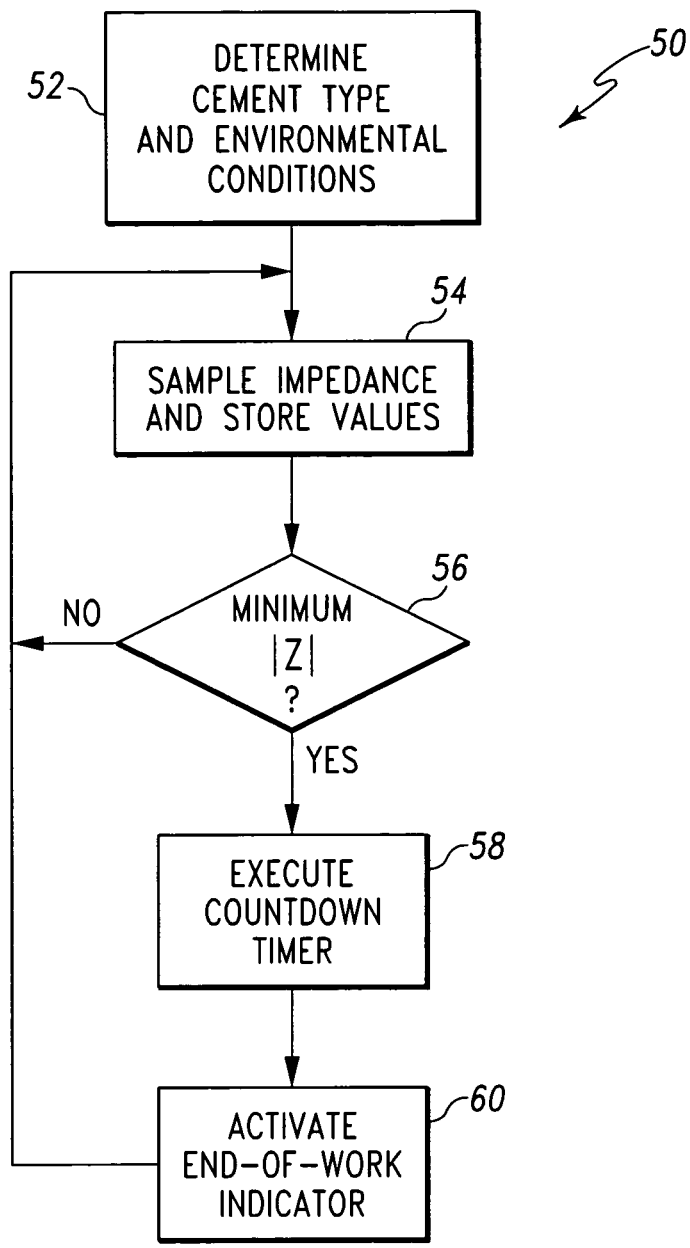
FIGS. 4-7 are flowcharts of a number of control routines which may be executed by the controller of the apparatus of FIG. 1.

Referring now to FIG. 4, there is shown an exemplary control routine 50 which may be executed by the controller 20 to predict the operating state of the curable bone cement composition 12 during an orthopaedic surgical procedure. Generally, the components of the bone cement composition 12 (i.e., the liquid component and the powder component) are first mixed together. The composition is thereafter monitored as it polymerizes. It should be appreciated that, as described above, the composition may be located in any type of container while it is being monitored. For example, the bone cement composition may be monitored while located in the syringe 14 or a mixing apparatus (not shown). Alternatively, a sample of the composition 12 may be placed in a sample vessel and thereafter monitored from the sample vessel. In any such case, the control routine 50 begins with step 52 in which variables and/or devices are initialized. In step 52, the processor 24 receives data from the input device 16 relating to the identity of the bone cement composition being monitored, and also scans or otherwise reads the output from the environmental sensor 17 to determine the environmental conditions (e.g., temperature and time) within the operating room. Armed with this information, the processor 24 selects the appropriate countdown timer profiles for use in predicting end-of-work time and setting time. More specifically, specific timer durations may be selected based on the type of bone cement composition to be used and the environmental conditions in the room. This may be done by selecting a specific timer profile from a large group of empirically generated profiles, or may be done by adding or subtracting time from a base timer profile based on the type of composition and the environmental conditions. It should be appreciated that the length of the countdown timer may be altered dynamically during the surgical procedure based on output from the environmental sensor 17. Alternatively, an initial adjustment (if any) may be made at device initialization with no further adjustments being made thereafter. Once the variables and/or devices have been initialized, the routine 50 advances to step 54.

Thereafter, the routine 50 advances to step 54 in which the impedance of the bone cement composition 12 is sampled. In particular, the processor 24 communicates with the impedance analyzer 32 to sample the complex impedance of the bone cement composition. The output from the impedance analyzer 32 is stored in the memory device 26. The data storage structure can be customized to the type of analysis to be performed on the data. For example, in some cases, all of the data points are maintained in the memory device 26 throughout the entirety of the orthopaedic procedure. In other cases, a predetermined number of points are stored in a FIFO buffer. In any case, the output of the impedance analyzer 32 is stored in the memory device 26 in step 54, and then the routine 50 advances to step 56.

In step 56, the processor 24 analyzes the stored data. For example, the processor 24 may compare the recent values to the historical values stored in the buffer to determine if a minimum magnitude of impedance value has been achieved in the manner described above. Alternatively, the processor 24 may determine the first derivative of the stored values to determine if a minimum magnitude of impedance value has been achieved in the manner described above. As such, in step 56 the processor 24 determines if the analyzed stored data indicates that the magnitude of impedance has decreased to a minimum value. If the magnitude of impedance of the bone cement composition 12 has decreased to a minimum value, a control signal is generated and the control routine 50 advances to step 58. If the magnitude of impedance of the bone cement composition 12 has not yet decreased to a minimum value, the control routine 50 loops back to step 54 to continue sampling the bone cement composition 12.

In step 58, a countdown timer is executed in response to the control signal generated in step 56. Once the countdown timer expires, the control routine 50 advances to step 60.

In step 60, the processor 24 generates a signal which activates the indicator 30 so as to generate a human-detectable signal. In the case of a visual indicator 30, one or more LED's may be illuminated to represent that the bone cement composition 12 has achieved end-of-work time. It should be appreciated that the LED's may be illuminated in a green-yellow-red succession to indicate, respectively, when it is acceptable to use the composition 12 (e.g., a green illumination when dough time has been achieved), when the composition 12 is nearing end-of-work time (e.g., a yellow illumination when end-of-work time is nearing), and when the composition 12 should no longer be used (e.g., a red illumination when end-of-work time has been achieved). The countdown timer may be used to determine when to illuminate the yellow LED, and then shift from yellow to red. In the case of an audible indicator 30, the processor 24 may cause the tone generator or voice generator to generate an audible indication in a similar manner.

After the human-detectable signal has been generated in step 60, the control routine 50 then loops back to step 54 to continue sampling the bone cement composition 12.

Figure 5:
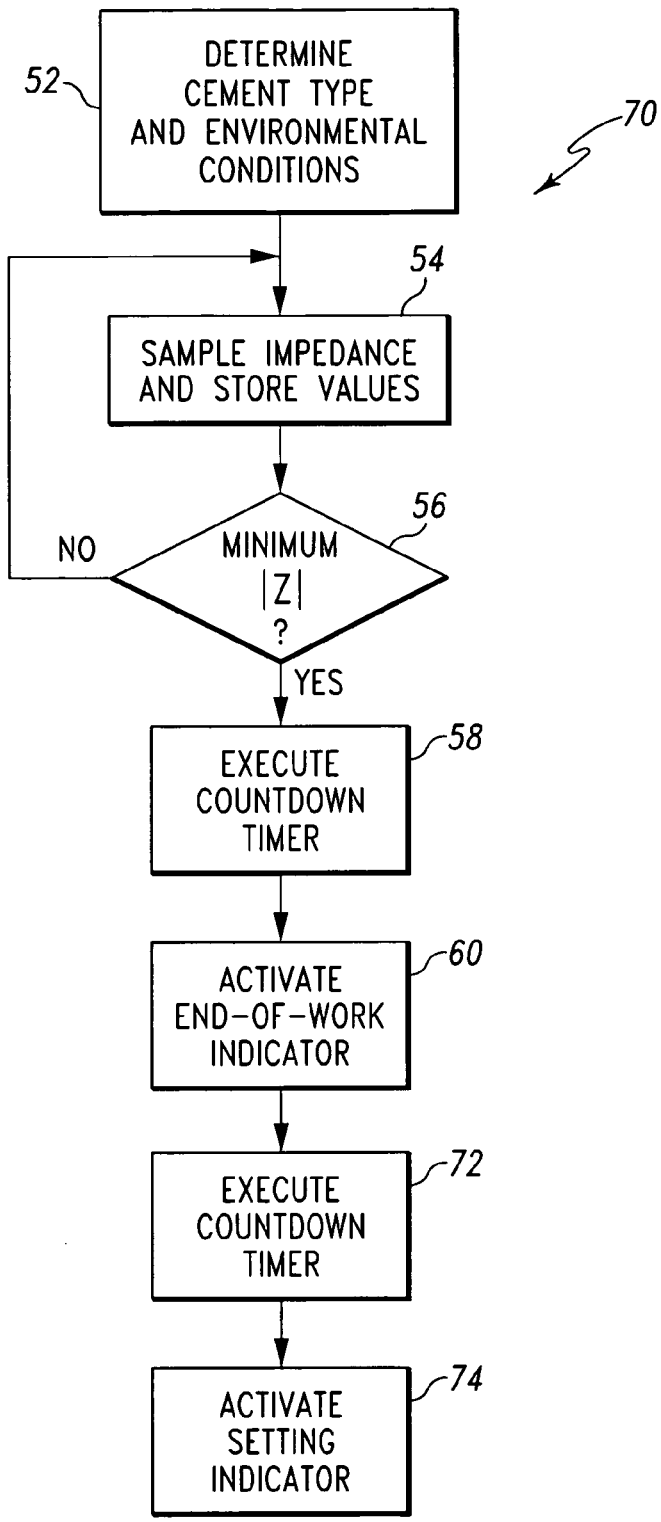

Referring now to FIG. 5, a control routine 70 is shown that is, in essence, the control routine 50 with the addition of an indication as to when setting time has been achieved. Steps 52-60 of the control routine 70 are identical to the similarly numbered steps of the control routine 50. However, subsequent to step 60, the control routine 70 does not loop back to step 54 (as does the control routine 50), but rather advances to step 72.

In step 72, a countdown timer is executed (or the countdown timer commenced in step 58 continues to count). This countdown timer is used to countdown the amount of time between when the minimum magnitude of impedance value is achieved (as determined in step 56) and the setting time of the bone cement composition 12. As described above, a single countdown timer may be used for both end-of-work time and setting time since both times are predicted from the same starting point (i.e., the point in time in which the minimum magnitude of impedance value is achieved). Alternatively, a separate countdown timer specific to setting time may be used. In any such case, once the countdown timer associated with setting time expires, the control routine 70 advances to step 74.

In step 74, the processor 24 generates a signal which activates the indicator 30 so as to generate a human-detectable signal. In the case of a visual indicator 30, one or more LED's may be illuminated to represent that the bone cement composition 12 has achieved setting time. It should be appreciated that the LED's may be illuminated in any desired manner to indicate when setting time has been achieved. In the case of an audible indicator 30, the processor 24 may cause the tone generator or voice generator to generate an audible indication in a similar manner.

Figure 6:
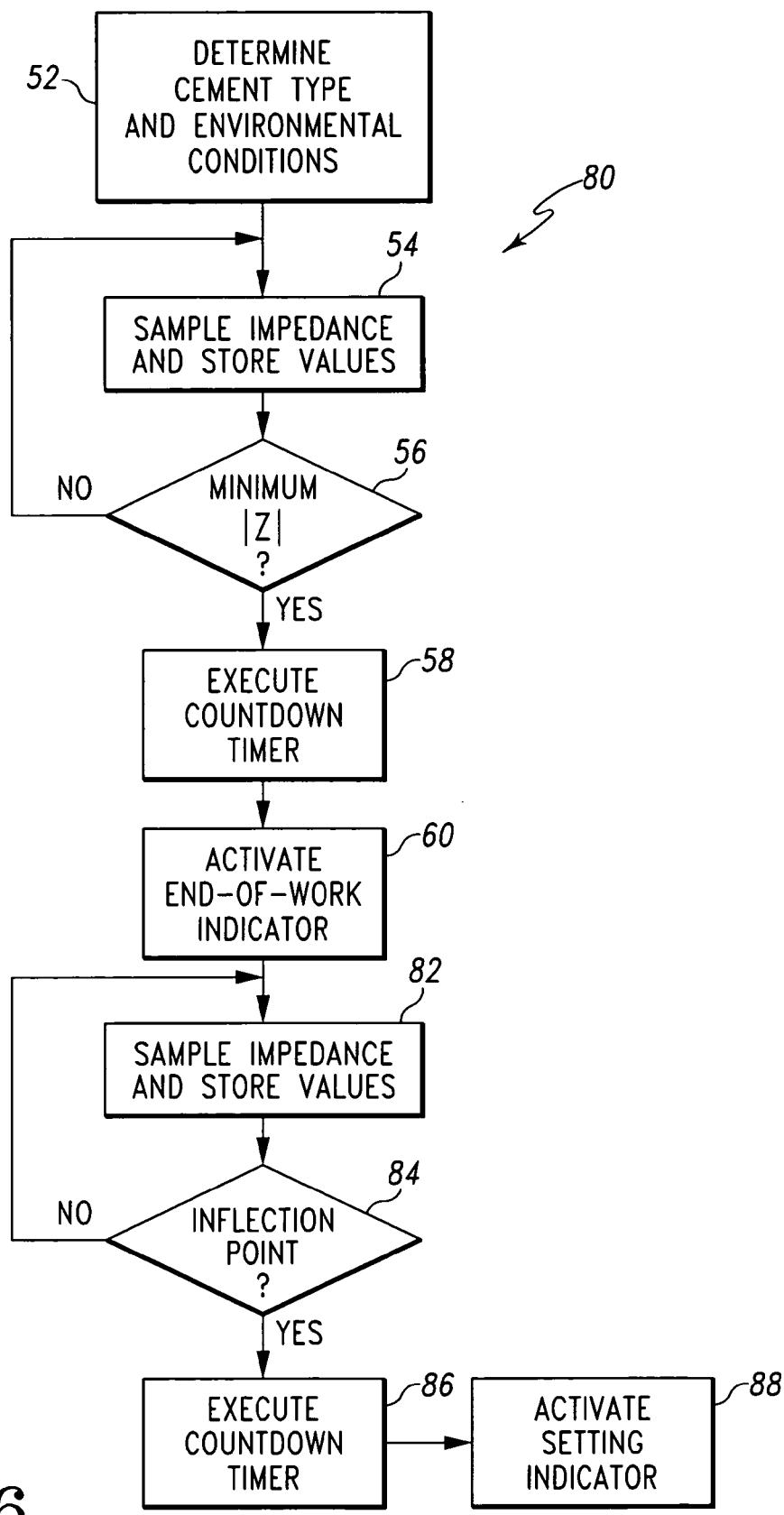

Referring now to FIG. 6, a control routine 80 is shown that is, in essence, the control routine 50 with the addition of another embodiment of an indication as to when setting time has been achieved. Steps 52-60 of the control routine 80 are identical to the similarly numbered steps of the control routine 50. However, subsequent to step 60, the control routine 80 does not loop back to step 54, but rather advances to step 82.

In step 82, the impedance of the bone cement composition 12 continues to be sampled. In particular, the processor 24 communicates with the impedance analyzer 32 to continue to sample or calculate the magnitude of the electrical impedance of the bone cement composition. The output from the impedance analyzer 32 is stored in the memory device 26 in a similar manner to as described above in regard to step 54. The routine 80 next advances to step 84.

In step 84, the processor 24 analyzes the stored impedance data to determine if an inflection point in the magnitude of impedance versus time plot has been achieved (with such a point being shown as point 46 on the plot of FIG. 2). To do so, the processor 24 may determine the second derivative of the stored values to determine if an inflection point has been achieved in the manner described above. As such, in step 82 the processor 24 determines if the analyzed data indicates that the magnitude of impedance has increased to an inflection point. If the magnitude of impedance of the bone cement composition 12 has increased to an inflection point, a control signal is generated and the control routine 80 advances to step 86. If the magnitude of impedance of the bone cement composition 12 has not yet increased to an inflection point, the control routine 80 loops back to step 82 to continue sampling the bone cement composition 12.

In step 86, a countdown timer is executed. This countdown timer is used to countdown the amount of time between when the inflection point is achieved (as determined in step 84) and the setting time of the bone cement composition 12. Once the countdown timer associated with setting time expires, the control routine 80 advances to step 88.

In step 88, the processor 24 generates a signal which activates the indicator 30 so as to generate a human-detectable signal. In the case of a visual indicator 30, one or more LED's may be illuminated to represent that the bone cement composition 12 has achieved setting time. It should be appreciated that the LED's may be illuminated in any desired manner to indicate when setting time has been achieved. In the case of an audible indicator 30, the processor 24 may cause the tone generator or voice generator to generate an audible indication in a similar manner.

Figure 7:
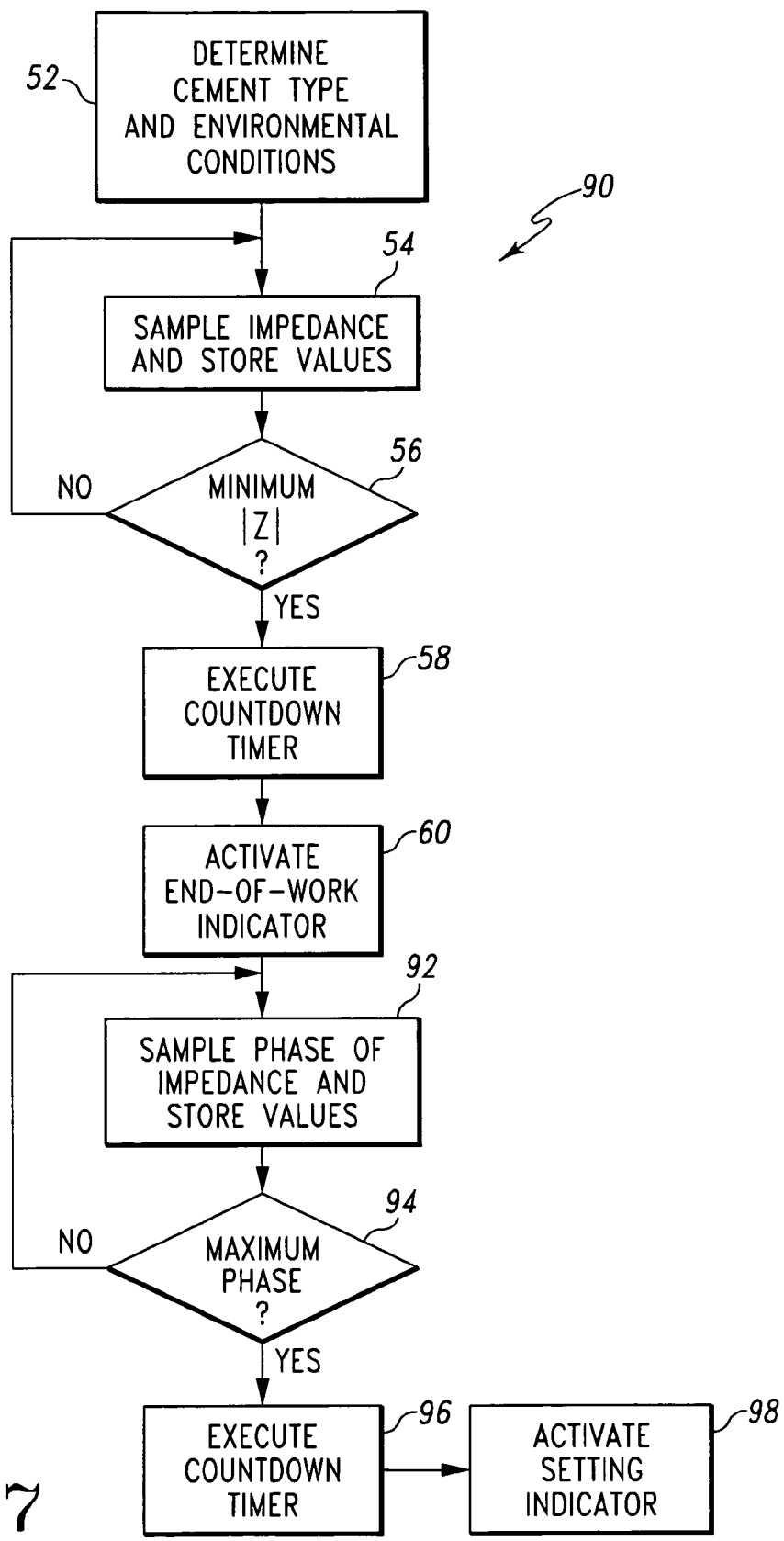

Referring now to FIG. 7, a control routine 90 is shown that is, in essence, the control routine 50 with the addition of another embodiment of an indication as to when setting time has been achieved. Steps 52-60 of the control routine 90 are identical to the similarly numbered steps of the control routine 50. However, subsequent to step 60, the control routine 90 does not loop back to step 54, but rather advances to step 92.

In step 92, the phase of impedance of the bone cement composition 12 is sampled. In particular, the processor 24 communicates with the impedance analyzer 32 to sample or calculate the phase of impedance of the bone cement composition. The output from the impedance analyzer 32 is stored in the memory device 26. The data storage structure can be customized to the type of analysis to be performed on the data. For example, in some cases, all of the data points are maintained in the memory device 26 throughout the entirety of the orthopaedic procedure. In other cases, a predetermined number of points are stored in a FIFO buffer. In any case, the output of the impedance analyzer 32 is stored in the memory device 26 in step 92, and then the routine 90 advances to step 94.

In step 94, the processor 24 analyzes the stored data. For example, the processor 24 may compare the recent values to the historical values stored in the buffer to determine if a maximum phase of impedance value has been achieved in the manner described above. Alternatively, the processor 24 may determine the first derivative of the stored values to determine if a maximum phase of impedance value has been achieved in the manner described above. As such, in step 94 the processor 24 determines if the analyzed data indicates that the phase of impedance has increased to a maximum phase of impedance value. If the phase of impedance of the bone cement composition 12 has increased to a maximum value, a control signal is generated and the control routine 90 advances to step 96. If the phase of impedance of the bone cement composition 12 has not yet increased to a maximum value, the control routine 90 loops back to step 92 to continue sampling the bone cement composition 12.

In step 96, a countdown timer is executed in response to the control signal generated in step 94. This countdown timer is used to countdown the amount of time between when the maximum phase of impedance value is achieved (as determined in step 94) and the setting time of the bone cement composition 12. Once the countdown timer expires, the control routine 90 advances to step 98.

In step 98, the processor 24 generates a signal which activates the indicator 30 so as to generate a human-detectable signal. In the case of a visual indicator 30, one or more LED's may be illuminated to represent that the bone cement composition 12 has achieved setting time. It should be appreciated that the LED's may be illuminated in any desired manner to indicate when setting time has been achieved. In the case of an audible indicator 30, the processor 24 may cause the tone generator or voice generator to generate an audible indication in a similar manner.

While the disclosure is susceptible to various modifications and alternative forms, specific exemplary embodiments thereof have been shown by way of example in the drawings and has herein be described in detail. It should be understood, however, that there is no intent to limit the disclosure to the particular forms disclosed, but on the contrary, the intention is to cover all modifications, equivalents, and alternatives falling within the spirit and scope of the disclosure.

There are a plurality of advantages of the present disclosure arising from the various features of the apparatus and methods described herein. It will be noted that alternative embodiments of the apparatus and methods of the present disclosure may not include all of the features described yet still benefit from at least some of the advantages of such features. Those of ordinary skill in the art may readily devise their own implementations of an apparatus and method that incorporate one or more of the features of the present disclosure and fall within the spirit and scope of the present disclosure.

For example, in addition to bone cement compositions, the methods and systems disclosed herein may be used to monitor other curable biomaterials or biocompatible materials.

The invention claimed is:

1. A method of predicting an operating state of a curable bone cement composition, the method comprising the steps of:

sampling the electrical impedance of the bone cement composition as the bone cement composition cures, generating a first electronic control signal if the magnitude of the electrical impedance of the bone cement composition has decreased to a minimum value, and generating a second electronic control signal if a predetermined amount of time has elapsed since generation of the first electronic control signal.

2. The method of claim 1, wherein the sampling step comprises exposing the bone cement composition to an electrical voltage or current at RF frequencies.

3. The method of claim 1, further comprising the step of generating a human-detectable audible signal in response to generation of the second electronic control signal.

4. The method of claim 1, further comprising the step of generating a human-detectable visual signal in response to generation of the second electronic control signal.

5. The method of claim 1, further comprising the step of generating, in response to generation of the second electronic control signal, a human-detectable signal indicating that a predetermined operating state of the bone cement composition has been achieved.

6. The method of claim 5, wherein the human-detectable signal generating step comprises generating a human-detectable signal indicating that end-of-work time of the bone cement composition has been achieved.

7. The method of claim 5, wherein the human-detectable signal generating step comprises generating a human-detectable signal indicating that setting time of the bone cement composition has been achieved.

8. The method of claim 1, further comprising the steps of:

generating a third electronic control signal if the magnitude of electrical impedance of the bone cement composition has increased from the minimum value to an inflection point, and generating a fourth electronic control signal if a predetermined amount of time has elapsed since generation of the third electronic control signal.

9. The method of claim 8, further comprising the step of generating, in response to generation of the fourth electronic control signal, a human-detectable signal indicating that a predetermined operating state of the bone cement composition has been achieved.

10. The method of claim 9, wherein the human-detectable signal generating step comprises generating a human-detectable signal indicating that setting time of the bone cement composition has been achieved.

11. The method of claim 1, further comprising the steps of:

generating a third electronic control signal if the phase of electrical impedance has increased to a maximum value, and generating a fourth electronic control signal if a predetermined amount of time has elapsed since generation of the third electronic control signal.

12. The method of claim 11, further comprising the step of generating, in response to generation of the fourth electronic control signal, a human-detectable signal indicating that a predetermined operating state of the bone cement composition has been achieved.

13. The method of claim 12, wherein the human-detectable signal generating step comprises generating a human-detectable signal indicating that setting time of the bone cement composition has been achieved.

14. The method of claim 1, wherein the second electronic control signal generating step comprises generating the second electronic control signal if a first predetermined amount of time has elapsed since generation of the first electronic control signal, further comprising the steps of:

generating, in response to generation of the second electronic control signal, a human-detectable signal indicating that end-of-work time of the bone cement composition has been achieved, generating a third electronic control signal if a second predetermined amount of time has elapsed since generation of the first electronic control signal, the second predetermined amount of time being greater than the first predetermined amount of time, and generating, in response to generation of the third electronic control signal, a human-detectable signal indicating that setting time of the bone cement composition has been achieved.

15. The method of claim 1, wherein the bone cement composition is located in a syringe during the sampling step.

16. An apparatus for predicting the operating state of a curable bone cement composition, the apparatus comprising:
a bone cement container,
an electrical impedance analyzer,
a processor electrically coupled to the electrical impedance analyzer, and
a memory device electrically coupled to the processor, wherein the memory device has stored therein a plurality of instructions which, when executed by the processor, cause the processor to:
operate the electrical impedance analyzer to sample the electrical impedance of the bone cement composition as the bone cement composition cures,
generate a first control signal if the magnitude of the electrical impedance of the bone cement composition has decreased to a minimum value, and
generate a second control signal if a predetermined amount of time has elapsed since generation of the first control signal.

17. The apparatus of claim 16, wherein the plurality of instructions, when executed by the processor, further cause the processor to operate the electrical impedance analyzer to expose the bone cement composition to an electrical voltage or current at RF frequencies.

18. The apparatus of claim 16, further comprising an audible tone generator electrically coupled to the processor, wherein the plurality of instructions, when executed by the processor, further cause the processor to operate the tone generator to generate a human-detectable audible signal in response to generation of the second control signal.

19. The apparatus of claim 16, further comprising a visual indicator electrically coupled to the processor, wherein the plurality of instructions, when executed by the processor, further cause the processor to operate the visual indicator to generate a human-detectable visual signal in response to generation of the second control signal.

20. The apparatus of claim 16, wherein the container comprises a syringe.

21. A method of predicting an operating state of a curable bone cement composition, the method comprising the steps of:
sampling the electrical impedance of the bone cement composition as the bone cement composition cures,
commencing a timer if the magnitude of the electrical impedance of the bone cement composition has decreased to a minimum value, and
generating a control signal if the timer reaches a predetermined time value.

22. The method of claim 21, wherein the sampling step comprises exposing the bone cement composition to an electrical voltage or current at RF frequencies.

23. The method of claim 21, further comprising the step of generating a human-detectable audible signal in response to generation of the control signal.

24. The method of claim 21, further comprising the step of generating a human-detectable visual signal in response to generation of the control signal.

25. The method of claim 21, further comprising the step of generating, in response to generation of the control signal, a human-detectable signal indicating that a predetermined operating state of the bone cement composition has been achieved.

26. The method of claim 25, wherein the human-detectable signal generating step comprises generating a human-detectable signal indicating that end-of-work time of the bone cement composition has been achieved.

27. The method of claim 25, wherein the human-detectable signal generating step comprises generating a human-detectable signal indicating that setting time of the bone cement composition has been achieved.

28. The method of claim 21, wherein the bone cement composition is located in a syringe during the sampling step.

29. An apparatus for predicting the operating state of a curable bone cement composition, the apparatus comprising:
a bone cement container,
an electrical impedance analyzer,
a processor electrically coupled to the electrical impedance analyzer, and
a memory device electrically coupled to the processor, wherein the memory device has stored therein a plurality of instructions which, when executed by the processor, cause the processor to:
operate the electrical impedance analyzer to sample the electrical impedance of the bone cement composition as the bone cement composition cures,
commence a timer if the magnitude of the electrical impedance of the bone cement composition has decreased to a minimum value, and
generate a control signal if the timer reaches a predetermined time value.

30. The apparatus of claim 29, wherein the plurality of instructions, when executed by the processor, further cause the processor to operate the electrical impedance analyzer to expose the bone cement composition to an electrical voltage or current at RF frequencies.

31. The apparatus of claim 29, further comprising an audible tone generator electrically coupled to the processor, wherein the plurality of instructions, when executed by the processor, further cause the processor to operate the tone generator to generate a human-detectable audible signal in response to generation of the control signal.

32. The apparatus of claim 29, further comprising a visual indicator electrically coupled to the processor, wherein the plurality of instructions, when executed by the processor, further cause the processor to operate the visual indicator to generate a human-detectable visual signal in response to generation of the control signal.

33. The apparatus of claim 29, wherein the container comprises a syringe.

* * * * *